United States Patent [19]

Röhrscheid

[11] 4,097,492
[45] Jun. 27, 1978

[54] PROCESS FOR THE PREPARATION OF NAPHTHALENE-1,4,5,8-TETRACARBOXYLIC ACID

[75] Inventor: Freimund Röhrscheid, Kelkheim, Taunus, Germany

[73] Assignee: Hoechst Aktiengesellschaft, Frankfurt am Main, Germany

[21] Appl. No.: 683,039

[22] Filed: May 4, 1976

Related U.S. Application Data

[63] Continuation-in-part of Ser. No. 501,665, Aug. 29, 1974, abandoned.

[30] Foreign Application Priority Data

Aug. 31, 1973 Germany .............................. 2343964

[51] Int. Cl.² ..................... C07D 311/02; C07C 51/33
[52] U.S. Cl. ............................... 260/345.2; 260/523 R
[58] Field of Search ............. 260/523 R, 524 N, 345.2

[56] References Cited

FOREIGN PATENT DOCUMENTS 751,484  1/1967  Canada .............................. 260/523 R
752,438  2/1967  Canada .............................. 260/523 R Primary Examiner—A. Siegel
Attorney, Agent, or Firm—Curtis, Morris & Safford

[57] ABSTRACT

Naphthalene-1,4,5,8-tetracarboxylic acid and typical derivative(s) thereof is (are) prepared by oxidation of periacenaphthindenones of the formula

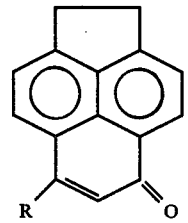

where R is H or lower alkyl, in a lower aliphatic carboxylic acid with nitric acid, optionally using also oxygen, in the presence of oxidation catalysts at temperatures above about 100° C; the reaction product being worked up in known manner. Naphthalene-1,4,5,8-tetracarboxylic acid is an important preliminary product for the manufacture of dyestuffs.

31 Claims, No Drawings

PROCESS FOR THE PREPARATION OF NAPHTHALENE-1,4,5,8-TETRACARBOXYLIC ACID

This application is a continuation-in-part of Ser. No. 501,665, filed Aug. 29, 1974, now abandoned.

The present invention relates to a process for the preparation of naphthalene-1,4,5,8-tetracarboxylic acid and derivative(s) thereof. Naphthalene-tetracarboxylic acid is an important preliminary product for dyestuffs. Its preparation in three steps, starting from pyrene, a process still applied in industry, is in principle described by Fierz David, Grundlegende Operationen der Farbenchemie, Vienna 1952:

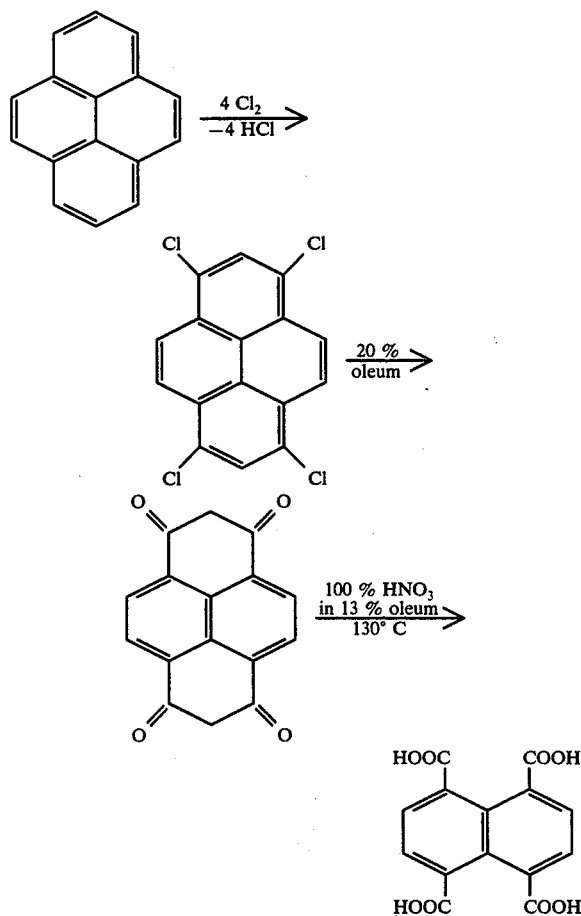

The yield of this process is about 50%, relative to the expensive pyrene. This synthesis produces large amounts of waste products the removal of which is expensive; for example, in the second step, 1850 kg of 20% oleum are used per 100 kg of halogenation product, which have to be worked up again.

It is the object of this invention to provide a more economic and rational preparation process. In accordance with the present invention, there is provided a process for the preparation of naphthalene-1,4,5,8-tetracarboxylic acid or the anhydride derivative thereof, which comprises oxidizing a peri-acenaphthindenone of the formula (I)

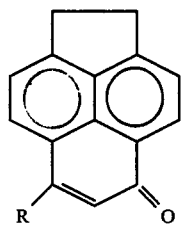

(I)

where R is hydrogen or alkyl having preferably from 1 to 4 carbon atoms, especially hydrogen or methyl, in an aliphatic carboxylic acid having preferably from 1 to 4 carbon atoms, especially acetic acid, as solvent, with nitric acid, optionally using also oxygen, in the presence of oxidation catalysts, at a temperature above about 100° C, isolating the reaction product obtained and optionally converting it to pure naphthalene-tetracarboxylic acid in known manner by alkaline recrystallization.

Among the starting products, which are known, the peri-acenaphthindenone-7 (R = H) can be obtained by treating the Na compound of the [β-oxyvinyl]- [acenaphthenyl -(5)-] -ketone with concentrated sulfuric acid (German Pat. No. 489,571). Peri-indenones of the formula (I), where R is alkyl, which are advantageously obtained according to German Offenlegungsschrift No. 2,229,692 by reaction of the corresponding β-ketocarboxylic acid fluoride with acenaphthene in liquid hydrogen fluoride, are for example the following compounds: 5-methyl-peri-acenaphthindenone-7, 5-ethyl-peri-acenaphthindenone-7, 5-propyl-peri-acenaphthindenone-7, 5-butyl-peri-acenaphthindenone-7.

The aliphatic carboxylic acid used as selective solvent or diluent may be employed in a concentration of more than about 50 weight %, preferably from 80 to 100 weight %, especially from 90 to 100 weight % (the remainder being water). The quantitative ratio is from about 1 to 10, preferably from 4 to 8 parts by weight of aliphatic carboxylic acid per part of peri-indenone. Acetic acid is preferably used. Other suitable aliphatic carboxylic acids are for example formic, propionic, or butyric acid. These acids are solvents in which, on the one hand, the compounds of formula (I) are soluble, so that the process starts from a homogeneous solution, but in which, on the other hand, the naphthalene-1,4,5,8-tetracarbocyclic acid or the anhydrides thereof, as compared to the other oxidation products, are insoluble, so that they precipitate and may easily be separated by filtration. Simultaneously, the aliphatic carboxylic acids are diluents for the nitric acid used, so that also concentrated nitric acid may be employed without causing a significant nitration.

In the case where oxygen is absent, the nitric acid is used in amounts of from about 7 to 14, preferably from 8 to 12 mols per mol of indenone. When elementary oxygen is simultaneously fed in, this molar ratio may be reduced to about 1 to 6, preferably 1.5 to 4, especially 2 to 4 mols. As indicated below, such elementary oxygen may be molecular oxygen mixed with nitrogen as occurs naturally in air, or may be in the pure form. In order to obtain a completely oxidized product, at least about 2 mols of $HNO_3$/mol of indenone should be employed. Products not completely oxidized may be after-oxidized in known manner after their isolation with $KMnO_4$ in alkaline solution. The nitric acid may be used in any concentration, but in order to avoid an unnecessary dilution of the solvent, that is, the carboxylic acid, there is advantageously employed concentrated, namely, at least 60%, preferably 90 to 100% HNO₃. batchwise, its amounts may be introduced into the vessel in one portion only, but preferably it is added in several portions or continuously.

As oxidation catalysts, those known from the literature may be used in known manner, especially catalysts of cobalt, manganese, copper, vanadium or molybdenum or their compounds, preferably in the form of, for example, their oxides, especially their salts. Thus, cobalt and manganese may be employed in the form of their nitrates, acetates or carbonates; vanadium in the form of, for example, ammonium vanadate, freshly precipitated vanadium pentoxide, or vanadly-acetylacetonate; molybdenum in the form of molybdenum hexacarbonyl, freshly precipitated molybdenum oxide, molybdenum tetrabromide, or hetero-polyacid with cobalt or manganese. The oxidation catalysts may be applied per se or, preferably, in combinations. Especially efficient are vanadium or a mixture of cobalt, manganese and vanadium. Surprisingly, the addition of small amounts of molybdenum compounds results in the obtention of a purer final product. The metal ion concentration in the case of cobalt and manganese is from about 0.2 to 40, preferably from 0.8 to 20, especially from 2 to 8 mg-atom/liter of carboxylic acid, that of vanadium is from about 0.2 to 40, preferably from 0.4 to 20, especially from 2 to 10 mg-atom/liter. A mixture of cobalt, manganese and vanadium yields especially high conversion rates with simultaneous high purity degree of the reaction product, for example a mixture of 2 mg-atom of cobalt, 2 mg-atom of manganese and 6–8 mg-atom of vanadium per liter of aliphatic carboxylic acid.

Small amounts of molybdenum (from 0.3 to 2 mg-atom/liter added to the above catalysts increase the oxidation rate. This is especially important in the case of semicontinuous or continuous processes, since already traces of incompletely oxidized products, which can be eliminated only with difficulty, adversely affect the quality of dyestuffs manufactured from the naphthalene-tetracarboxylic acid.

When nitric acid and oxygen are simultaneously used, the oxygen may be fed in in pure form or in admixture with an inert gas, for example with nitrogen (as air). In order to obtain a pure tetra-acid product, the oxygen amount should be at least equivalent to the stoichiometric amount required with consideration of the nitric acid used. Since the oxidation in the case, for example, of 5-methyl-peri-acenaphthindenone-7, according to the following reaction scheme (based on the dianhydride being the sole reaction product)

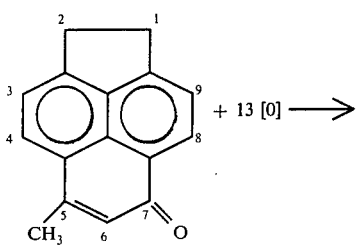

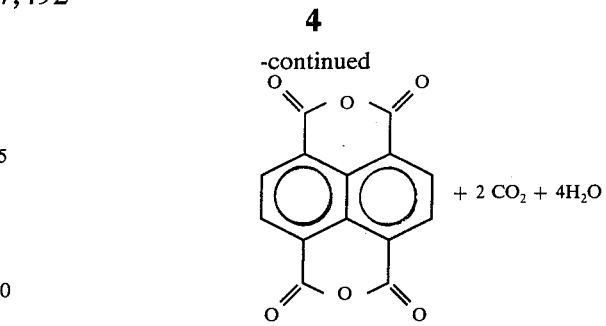

requires 13 oxygen equivalents, a stoichiometric oxygen amount of 4.5 mols per mol of indenone, or about 100 normal liters (at normal pressure and temperature) of O₂ are employed, when for example, 2 mols of HNO₃ are used (degradation to N₂O and H₂O). Generally, however, an oxygen excess of from about 10 to 400% or more is used; the upper limit not being critical. Preferably, from about 20 to 200% of oxygen excess are employed, the oxygen excess being nearer to the upper limit when air is used.

The reaction is carried out above about 100° C, and advantageously in a temperature range of from about 120 to about 240° C, preferably from 140° to 200° C, especially from 150° to 180° C. When operating continuously, the preferred temperatures are in the upper range of the cited intervals.

The reactor pressure is chosen, in known manner, above the vapor pressure of the aliphatic carboxylic acid at the reaction temperature, that is, generally, above 2 absolute atmospheres. There is no critical upper limit; this limit depending substantially on the technological conditions. Depending on the reaction temperature, a pressure of from 3 to 30, especially from 4 to 20 absolute atmospheres is chosen, which pressure may be easily controlled in the case of a corresponding introduction of oxygen by adjusting the waste gas valve.

The process may be carried out batchwise or continuously. In the first case, all reactants may be introduced into the vessel and heated to reaction temperature, while oxygen is passed through. When large amounts of naphthalene-tetracarboxylic acid are prepared, it is recommended to pump in the nitric acid during the reaction only and to that extent to which it is consumed, so that its stationary concentration is kept as low as possible, thus avoiding nitration of the naphthalene ring and formation of possibly explosive mixtures of organic compounds and nitric acid.

When the naphthalene-tetracarboxylic acid is prepared batchwise, the process is carried out as follows: The solutions of peri-indenone and HNO₃ in, for example, acetic acid are pumped, simultaneously but separately, into the reactor, in which there are already the metal catalyst and acetic acid heated to the desired reaction temperature. The nitric acid may also be fed in without being diluted by acetic acid. The metal catalyst, in the form of a solution or dispersion in the carboxylic acid may also be fed in by means of a third pump. It is very important for the reaction to proceed as desired that during the total reaction time an intense intermixing of the reactants in the liquid or gaseous phase is ensured, which can be achieved for example by thorough agitation of the reaction mixture and/or passing the required oxygen through the vessel. It is also possible to use shaking reactors. Especially suitable materials for the walls of pressure reactors are for example tantalum, titanium or enamel. The reaction temperature should be at least from about 120° to 140° C, since lower temperatures, for example of from 100° to 120° C, sometimes do not incite the heavily exothermal oxidation reaction, which may cause an uncontrollable heat accumulation when the reaction finally starts. During the operations of pumping in the reactants, oxygen is fed in in an amount 1 to 1.5 times greater than that theoretically required, and simultaneously, waste gas is discharged via a cooler, in order to eliminate the $CO_2$, CO, $N_2$ and $N_2O$ formed and to maintain the reaction pressure. Already at 150° C, the reaction proceeds rapidly and nearly completely, so that the pumping operations may take only about 2 hours. Subsequently, the temperature is advantageously raised to 150°–170° C with further feeding-in of oxygen, and after a time of, for example, from 30 minutes to 3 hours, optionally with addition of a small amount of nitric acid, intermediate products not yet completely oxidized before are converted. Immediately after the start of the reaction, there is a high percentage of $N_2O$ in the waste gas besides less $N_2$, a small amount of CO and much $CO_2$ (see Table 1). After the reaction is complete, generally more than 99% of the nitric acid are consumed.

The controlled dosage of the nitric acid ensures stationary concentration of $HNO_3$ and $NO_2$ in the reactor to be unimportant, which results in a lower degree of reactor wall corrosion than that to be expected using the mixture of nitric and acetic acid.

The reaction may be carried out continuously by cascade-connecting several reactors, in order to better utilize the oxygen.

The reaction product (its greater part being microcrystalline naphthalene-tetracarboxylic anhydride or dianhydride in, for example, acetic acid) is discharged by suction-filtration or centrifugation, washed with acetic acid and dried.

For purification and complete conversion to naphthalene-1,4,5,8-tetracarboxylic acid, the reaction product may be dissolved in alkali, preferably in dilute sodium hydroxide solution, and reprecipitated with an acid, preferably hydrochloric or sulfuric acid, in the form of naphthalene-tetracarboxylic acid. In order to prevent a recurrent formation of anyhdride, especially the latter operation is carried out at low temperature, preferably at room temperature.

In many cases, however, the crude product may be used without any work-up. For determining the quality, it may be converted to indanthrene-scarlet with o-phenylenediamine. From the dyestuff yield obtained, the crude yield may be calculation-converted to naphthalene-tetracarboxylic dianhydride. The dianhydride data indicated in the Examples are obtained in this manner.

The acetic acid or the aliphatic carboxylic acid of the filtrate may be reused as reaction medium. Since it is practically free from nitric acid, the reaction water may be safely eliminated by distillation; for example, a mixture of 97% of water and 3% of acetic acid may be distilled off and subsequently, the acetic acid per se may optionally be distilled over in pure form.

As compared to the known process (pyrene), the process of the invention must be considered as a considerable progress in the art, since a cheaper and easily available starting material (especially 5-methyl-peri-acenaphthindenone-7) is used and a good yield of very pure final product is obtained. Its special advantage resides in the fact that waste products which can be worked up only with difficulty or pollute the environment are nearly absent. Furthermore, the combined use of $HNO_3$ and oxygen requires only relatively small amounts of nitric acid, thus saving cost, reducing considerably the risk of explosions and ensuring a better utilization of the reactor volume, which factors make the process very economic.

The process is new and it is surprising that it can be realized. Although it is known to oxidize alkylated aromatic compounds with oxygen and/or nitric acid to form aromatic carboxylic acids, those processes, because of the special chemical properties of peri-acenaphthindenones of formula I, failed whenever it was tried to obtain naphthalene-tetracarboxylic acid from these compounds.

As is known, the "Amoco" process is especially efficient for the oxidation with oxygen on air, according to which process terephthalic acid is prepared by oxidation of p-xylene with air in 95% acetic acid at 190°–205° C. The reaction pressure of this process is from 12 to 28 atm/g. As catalyst, there is used a combined system of cobalt acetate, manganese acetate, tetrabromo-ethane and ammonium bromide (German Auslegeschrift No. 1,081,445 and U.S. Pat. No. 2,962,361). According to this process, for example, acenaphthene may be oxidized to 1,8-nephthalene-dicarboxylic acid. When this process was applied to 5-methyl-peri-acenaphthindenone-7, there was no formation of nephthalene-tetracarboxylic acid, but black micro-crystals insoluble in glacial acetic acid and soluble in alkali, corresponding to the formula $C_{16}H_6O_5$ having the following structure

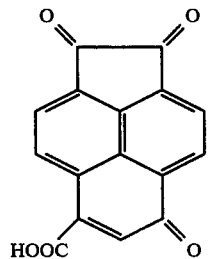

were obtained.

The oxidation of alkyl-aromatic compounds by means of dilute aqueous $HNO_3$ is already described, for example for xylenes in German Pat. Nos. 820,308 and 1,051,840, for p-cymene and p-di-isopropylbenzene in German Auglegeschrift No. 1,046,017 and German Pat. No. 1,155,111. The oxidation of these compounds yields terephthalic acid. In the examples disclosed, temperatures of from 240° to 260° C are required for the oxidation of p-xylene, from 260° to 280° C for the oxidation of p-cymene and p-di-isopropylbenzene. At these high temperatures, simultaneously high pressures of from 50 to 100 absolute atmospheres establish themselves, which require expensive pressure apparatus. Furthermore, the nitric acid concentration should be at least 10%, because only then the oxidation can be completed within a reasonable time. This fact and the high temperatures require very resistant reactor materials. Operations under these conditions are very difficult and complicated.

These known processes, however, cannot be applied to the peri-indenones of formula I, since the compounds decompose at the high temperatures required, and the extreme oxidation conditions cause a degradation of the naphthalene skeleton to the benzene nucleus. 5-methyl-peri-acenaphthindenone-7, because of its 4 C-C bonds to be split, may be approximately compared to p-di-isopropylbenzene. While, however, according to the indications given in German Patent No. 1,155,111, p-di-isopropylbenzene must be oxidized at 260°–280° C with 40% aqueous nitric acid, it is possible according to the process of the invention to oxidize 5-methyl-peri-acenaphthindenone-7 to naphthalene-tetracarboxylic dianhydride in a smoothly proceeding reaction with only 2 weight % of nitric acid in glacial acetic acid and already at 135°–145° C. This especially remarkable, since oxidation degradation and splitting of the alkyl groups of, for example, 5-methly-peri-acenaphthindenone-7 is considerably more difficult than in the case of p-di-isopropylbenzene, because the starting product contains two condensed rings. There is therefore always the risk of the oxidation being stabilized on the intermediate ketone or di-ketone step, as this is the case when the oxidation is carried out with oxygen alone in the presence of metal catalysts.

This proves that the oxidation of peri-acenaphthindenones of formula I is not analogous to the oxidation of simple alkylated aromatic compounds such as toluene, xylene or di-isopropylbenzene, but that this class of compounds required new reaction possibilities to be found and new reaction conditions to be developed.

Moreover, the composition of the waste gases show that there are obviously peculiar differences in the reaction mechanisms of the oxidation of indenones in glacial acetic acid with nitric acid and oxygen in the presence of oxidation catalysts and the oxidation of alkyl-aromatic compounds with aqueous nitric acid. In the following Table 1, a waste gas (A) from the oxidation of p-di-isopropylbenzene with 40% nitric acid at 260° C (German Pat. No. 1,155,111) is compared with a waste gas (B) according to the process of the invention (Example 7). The indicated values are in % by volume.

TABLE 1

| | $O_2$ | $NO_2$ | NO | $N_2O$ | $N_2$ | CO | $CO_2$ |
|---|---|---|---|---|---|---|---|
| A | — | 14.0 | 58.0 | 0.9 | 4.0 | 4.0 | 19.1 |
| B | 25.0 | 0.2 | 0.0 | 11.3 | 7.5 | 5.4 | 50.6 |

The table shows that in the case of the process of the invention the consumption of nitric acid is practically quantitati even in the presence of excess oxygen, and that substantially $N_2O$ and $N_2$ are formed.

The following examples illustrate the invention:

EXAMPLE 1

In a standing autoclave lined with chromium/nickel/molybdenum steel (Remainit HC) and provided with a magnetic agitator, 800 ml of glacial acetic acid, 1.5 g of cobalt acetatetetrahydrate, 50 g of 5-methyl-peri-acenaphthindenone-7 (80%) and 31.5 g of pure nitric acid were introduced. The feeding rate of oxygen was adjusted by means of the gas inlet valve to 10 Nl/h (Nl/h = normal liters of gas per hour), the pressure by means of the waste gas valve to 11 absolute atmospheres, and subsequently, the batch was heated to the reaction temperature of 150° C with agitation. The waste gas (about 10 Nl/h) was taken off via a pressure cooler and measured by means of a gas meter. After 4 hours, the reaction mixture was cooled, the vessel was depressurized and the contents of the autoclave were filtered. The filter residue was washed with acetic acid and dried at 80° C/150 torrs. The yield was 28.7 g of ocheryellow powder, corresponding to 25.3 g of naphthalene-tetracarboxylic dianhydride (51.3%).

Typically the dianhydride product in these examples includes at least minor amounts of the mono-anhydride and of the tetracarboxylic acid derivatives. Thus crude naphthalene-tetracarboxylic acid product is preferably converted into pure naphthalene-1,4,5,8 tetracarboxylic as shown in Example 11.

Comparative Example 1 (Amoco process)

900 ml of glacial acetic acid, 1.3 g of cobalt acetate-tetrahydrate, 2.6 g of manganese acetate-tetrahydrate, 0.3 g of ammonium bromide, 2.0 g of tetrabromo-ethane and 50 g of 5-methyl-peri-acenaphthidenone-7 (88%) were introduced into an autoclave as described in Example 1. Operations were carried out as indicated in Example 1. The reaction temperature was 210° C, the pressure 14 absolute atmospheres, the reaction time 10 hours, the oxygen and waste gas amount about 5 Nl/h. The yield of reaction product was 45.9 g of a black powder which was insoluble in glacial acetic acid and soluble in alkali, and which, according to elementary analysis, IR spectrum and titration had the formula $C_{16}H_6O_5$ and the following structure:

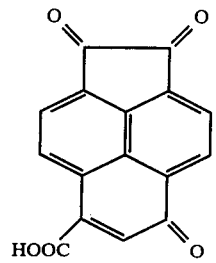

EXAMPLE 2:

800 ml of glacial acetic acid, 1.5 g of cobalt acetate-tetrahydrate, 3.0 g of ammonium-metavanadate, dissolved in 30 g of pure nitric acid, and 50 g of 5-methyl-peri-acenaphthindenone-7 (92%) were introduced into an autoclave as described in Example 1, and operations were carried out as indicated in Example 1. The reaction temperature was 150° C, the pressure 11 absolute atmospheres, the reaction time 5.5 hours and the oxygen and waste gas amount about 10 Nl/h.

The yield was 39.1 g of ocher colored small cyrstals, corresponding to 35.6 g of naphthalene-tetracarboxylic dianhydride (63.4%).

EXAMPLE 3:

800 ml of glacial acetic acid, 1.0 g of ammonium-metavanadate dissolved in 30 g of pure nitric acid, and 50 g of 5-methyl-peri-acenaphthindenone-7 (93%) were introduced into an autoclave as described in Example 1, and operations were carried out as indicated in Example 1. The reaction temperature was 150° C, the pressure 5 absolute atmospheres, the reaction time 3.5 hours, the amount of oxygen and waste gas about 10 Nl/h.

The yield was 33.5 g of ocher-brown fine crystals, corresponding to 30.1 g of naphthalene-tetracarboxylic dianhydride (53.2%).

EXAMPLE 4

As described in Example 1, 800 ml of glacial acetic acid, 1.0 g of ammonium metavanadate dissolved in 30 g of pure nitric acid, and 50 g of 5-methyl-peri-acenaphthindenone-7 (95%) were introduced into the autoclave and oxidized. The reaction temperature was 180° C, the pressure 11 absolute atmospheres, the reaction time 2.5 hours and the amount of oxygen and waste gas about 10 Nl/h.

The yield was 44.4 g of ocher colored fine crystals, corresponding to 40.7 g of naphthalene-tetracarboxylic dianhydride (70.5%).

EXAMPLE 5

As described in Example 1, 800 ml of glacial acetic acid, 1.0 g of ammonium metavanadate dissolved in 30 g of pure nitric acid, and 50 g of 5-methyl-peri-acenaphthindenone-7 (92%) were introduced into the autoclave and oxidized. The reaction temperature was 210° C, the pressure 11 absolute atmospheres, the reaction time 2 hours and the amount of oxygen and waste gas about 10 Nl/h. The yield was 39.8 g of oliveocher fine crystals, corresponding to 36.1 g of naphthalene-tetracarboxylic dianhydride (64.2%).

EXAMPLE 6

300 ml of glacial acetic acid and 1.0 g of vanadyl-acetyl-acetonate were introduced into an autoclave as described in Example 1, and subsequently heated to 160° C with agitation. Via a pump A (pump and feeding duct heated to 70° C), 50 g of 5-methyl-peri-acenaphthindenone-7 (96%) dissolved in 400 ml of glacial acetic acid, and via a pump B, 30 g of $HNO_3$ in 200 ml of glacial acetic acid were fed in uniformly and simultaneously within one hour. The pressure was kept at 8 absolute atmospheres, and the amount of oxygen and waste gas was about 20 Nl/h. Subsequently, agitation was continued for 1.5 hours under the same conditions. The yield was 44.7 g of a light ocher, crystalline powder, corresponding to 42.0 g of naphthalene-tetracarboxylic dianhydride (71.7%). The absolute residual amount of $HNO_3$ in the glacial acetic acid was 0.24 g. A waste gas sample taken in the first hour had the following composition:

|         | $O_2$ | $NO_2$ | $N_2O$ | $N_2$ | CO  | $CO_2$ |
|---------|-------|--------|--------|-------|-----|--------|
| % by vol. | 60  | 0.2    | 6.0    | 3.3   | 3.2 | 29     |

EXAMPLE 7

As described in Example 6, there were introduced: 300 ml of glacial acetic acid, 1.0 g of cobalt acetate-tetrahydrate, 1.0 g of manganese acetate-tetrahydrate, 2.0 g of vanadyl-acetylacetonate. Within 2 hours, 200 g of 5-methyl-peri-acenaphthindenone-7 (93.5%) in 500 ml of acetic acid were pumped in via pump A, and 120 g of $HNO_3$ (96%) in 240 ml of acetic acid via pump B. The reaction temperature was 140° C, the pressure 10 absolute atmospheres. The amount of oxygen and waste gas was adjusted at about 50 Nl/h. After the substances were pumped in, the temperature was raised to 170° C, and agitation was continued for a further 3 hours at an amount of oxygen and waste gas of about 20 Nl/h.

The yield was 179 g of a powder having a very light ocher color, which corresponds to 168.5 g of naphthalene-tetracarboxylic dianhydride (73.9%). The absolute residual amount of $HNO_3$ in the glacial acetic acid was 0.9 g. A waste gas sample taken during the pumping operations had the following composition:

|         | $O_2$ | $NO_2$ | $N_2O$ | $N_2$ | CO  | $CO_2$ |
|---------|-------|--------|--------|-------|-----|--------|
| % by vol. | 25.0 | 0.2  | 11.3   | 7.5   | 5.4 | 50.6   |

EXAMPLE 8

As described in Example 6, there was introduced: 300 ml of glacial acetic acid, 0.5 g of cobalt acetate-tetrahydrate, 0.5 g of manganese acetate-tetrahydrate, 2.0 g of vanadyl-acetyl-acetonate and 0.2 g of molybdenum-hexacarbonyl. Within 3 hours, 200 g of 5-methyl-peri-acenaphthindenone-7 (95%) in 400 ml of glacial acetic acid were pumped in via pump A, and 120 g of $HNO_3$ (96%) in 240 ml of glacial acetic acid via pump B. The reaction temperature was 135° C, the pressure 7 absolute atmospheres. The amount of oxygen and waste gas was adjusted at about 60 Nl/h. After the substances had been pumped in, the reaction temperature was raised to 145° C and agitation was continued for a further 2 hours at an amount of oxygen and waste gas of about 15 Nl/h. The yield was 164.2 g of ocher colored powder, corresponding to 153.8 g of naphthalene-tetracarboxylic dianhydride (66.3%).

EXAMPLE 9

(Oxidation with $HNO_3$ without oxygen)

As described in Example 6, there were introduced 300 ml of glacial acetic acid, 1.5 g of cobalt acetate-tetrahydrate, 1.5 g of manganese acetate-tetrahydrate, 1.5 g of vanadyl-acetyl-acetonate. Within 2 hours, there were pumped in via pump A 50 g = 0.227 mols of 5-methyl-peri-acenaphthindeone-7 (90%) in 500 ml of glacial acetic acid and via pump B 114 g = 1.82 mols of $HNO_3$ in 240 ml of glacial acetic acid. The reaction temperature was 150° C. The pressure mounted during the reaction and was kept constant at 11 absolute atmospheres by taking off waste gas. After termination of the pumping operations, agitation was continued for about 20 minutes under the same conditions.

The yield was 32.9 g of brown powder, corresponding to 28.7 g of naphthalene-tetracarboxylic dianhydride (52.3%). The absolute residual amount of $HNO_3$ in the glacial acetic acid was 1.3 g.

EXAMPLE 10

(Oxidation with $HNO_3$ and air)

As described in Example 6, there were introduced: 300 ml of glacial acetic acid, 1.5 g of cobalt acetate-tetrahydrate, 1.5 g of manganese acetate-tetrahydrate, 1.5 g of vanadyl-acetyl-acetonate, 0.1 g of molybdenum-hexacarbonyl. Within 3 hours, 200 g of 5-methyl-peri-acenaphthindenone-7 (90%) in 500 ml of glacial acetic acid were pumped in via pump A, and 120 g of $HNO_3$ in 240 ml of glacial acetic acid via pump B. The reaction temperature was 140° C, the pressure 15 absolute atmospheres. Instead of pure oxygen, air was used, and the amount of air and waste gas was adjusted to about 350 Nl/h. After termination of the pumping operations, the reaction temperature was raised to 170° C, and agitation was continued for a further 2 hours at an amount of air and waste gas of 50 Nl/h. The yield was 168.2 g of ocher colored, finely crystallized powder, corresponding to 157.3 g of naphthalene-tetracarboxylic dianhydride (71.6%).

EXAMPLE 11

10 g of the crude naphthalene-tetracarboxylic acid product obtained according to Example 6 were suspended in 300 ml of water at room temperature, a solution of 6 g of NaOH in 100 ml of water was added, the mixture was then heated to boiling temperature and filtered hot through a plaited filter for the obtention of a clear solution. After cooling of the filtrate to room temperature, an about 20% aqueous hydrochloric acid solution was added with agitation until the solution had a pH of 1. After a 2 hours standing of the mixture, the crystallized product was suction-filtered, washed with water and dried at room temperature over calcium chloride. 10.8 g of pure naphthalene-1,4,5, 8-tetracarboxylic acid having a weakly ocher color were obtained.

EXAMPLE 12

800 ml of glacial acetic acid, 50 g of 5-methyl-peri-acenaphthindenone-7 (93%) and a solution of $VCl_3$ in nitric acid were introduced into an autoclave as described in Example 1, and operations were carried out as in said Example. The solution of $VCl_3$ was obtained by mixing a solution of 1.3 g of $VCl_3$ in 10 ml $H_2O$ with 30 g of pure nitric acid. The reaction temperature was 180° C, the pressure 11 absolute atmospheres, the reaction time 3 hours, and the oxygen and waste gas amount about 10 Nl/h.

The yield was 43.7 g of ocher colored small crystals corresponding to 39.7 g of naphthalene-tetracarboxylic dianhydride (70.2% of the theory).

EXAMPLE 13

800 ml of glacial acetic acid, 1.8 g of $V(CO)_6$, 50 g of 5-methyl-peri-acenaphthindenone-7 (93%) and 32 g of pure nitric acid were introduced into an autoclave and oxidized as described in Example 1. The reaction temperature was 170° C, the pressure, reaction time, oxygen and waste gas amount as in Example 12.

The yield was 44.1 g of ocher colored small crystals corresponding to 39.9 g of naphthalene-tetracarboxylic dianhydride (70.5%).

EXAMPLE 14

800 ml of glacial acetic acid, 50 g of 5-methly-peri-acenaphthindenone-7 (93%) and a solution of freshly precipitated $V_2O_5$-hydrate (0.9 g $V_2O_5$) in 32 g of pure nitric acid were introduced into an autoclave and oxidized as described in Example 1. The $V_2O_5$-hydrate was obtained by dissolving 1.22 g (0.01 mols) of sodium meta-vanadate in 10 ml $H_2O$ and precipitation with 10 ml 1-n-nitric acid.

The precipitated red-brown $V_2O_5$-hydrate was filtered, washed with 5 ml $H_2O$ and used in this state.

The reaction temperature was 180° C, the pressure 11 absolute atmospheres, the reaction time 2 hours, and the oxygen and waste gas amount about 10 Nl/h.

The yield was 44.1 g of ocher colored small crystals, corresponding to 40.5 g of naphthalene-tetracarboxylic dianhydride (71.6%).

EXAMPLE 15

0.24 g $KMnO_4$ were added to a solution of 1.44 g $Mn(OOCCH_3)_2 \cdot 4H_2O$ in 15 ml glacial acetic acid under stirring. The resulting brown solution of $Mn(OOCCH_3)_3$ in glacial acetic acid was filled into an autoclave together with 300 ml glacial acetic acid, 1.5 g $Co(OOCCH_3)_2 \cdot 4H_2O$, and a solution of 1 g of ammonium-meta-vanadate $NH_4VO_3$ in 10 ml of pure (100%) nitric acid. The batch was heated to 160° C with agitation. By means of a pump A there was added to the batch a solution of 200 g of 5-methyl-peri-acenaphthindenone-7 (93%) in 500 ml of glacial acetic acid and by means of a second pump B a mixture of 120 g nitric acid and 240 ml glacial acetic acid smoothly and simultaneously during three hours. The reaction temperature was 160° C, the pressure 11 absolute atmospheres. The oxygen and waste gas amount was adjusted to 70 Nl/h. 30 minutes after finishing the metering of the contents of both pumps A and B into the autoclave, the reaction mixture was allowed to cool. After filtration, 173.3 g of an ocher colored powder corresponding to 162.1 g of naphthalene-tetracarboxylic dianhydride (71.7%) were obtained.

As a source for $Mn^{+3}$-ions there can be used also freshly precipitated $MnO_2$ and $KMnO_4$ for instance, since these compounds are rapidly reduced to the $Mn_{+3}$ state by 5-methyl-peri-acenaphthindenone-7.

I claim:

1. A process for the preparation of a mixture of naphthalene-1,4,5,8-tetracarboxylic acid and its anhydrides, which comprises oxidizing a peri-acenaphthindenone of the formula

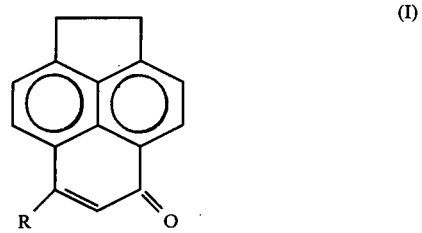

where R is hydrogen or lower alkyl, in acetic, formic, proprionic, or butyric acid as a solvent present in a concentration of about 1 to 10 parts by weight per part of said indenone, with nitric acid in the absence of oxygen in an amount from about 7 to about 14 mols per mol of said indenone or with nitric acid in the presence of oxygen in an amount from 1 to about 6 mols per mol of said indenone, in the presence of an oxidation catalyst, said catalyst being present in an effective amount having a concentration on the order of about 0.2 to 40 mg-atom/l of said solvent at a temperature from above about 100° C to about 240° C, and isolating the reaction product obtained.

2. A process as claimed in claim 1, wherein said catalyst is an oxidation catalyst of cobalt, manganese, copper, vanadium, molybdenum, their salts or oxides, or mixtures thereof.

3. A process as claimed in claim 2, which comprises a reaction temperature from 140° C to 200° C.

4. A process as claimed in claim 2, which comprises a reaction temperature of about 120° to about 240° C.

5. A process according to claim 4, which comprises said catalysts being in the form of oxides.

6. A process as claimed in claim 4, which comprises said catalysts being in the form of salts.

7. A process as claimed in claim 4, which comprises alkaline recrystallizing conversion and purification for naphthalene-tetracarboxylic acid by dissolving the reaction product in alkali and reprecipitation with an acid.

8. A process as claimed in claim 7, which comprises said alkali being sodium hydroxide and said re-precipitating acid being hydrochloric or sulfuric.

9. A process as claimed in claim 4, which comprises said nitric acid being added to said reaction in a concentration of at least 60%.

10. A process as claimed in claim 4, wherein said reaction pressure is above the vapor pressure of said carboxylic acid.

11. A process as claimed in claim 4, which comprises said nitric acid being present in an amount of from about 8 to 12 mols per mol of said indenone and said reaction being in the practical absence of an oxygen containing gas.

12. A process as claimed in claim 4, which comprises said nitric acid being used in an amount of from about 2 to 4 mols per mol of said indenone.

13. A process as claimed in claim 4, which comprises use of an excess of the stoichiometric oxygen amount of about 10 to about 400%.

14. A process as claimed in claim 4, wherein said catalyst comprises cobalt acetate tetrahydrate.

15. A process as claimed in claim 14, wherein said catalyst further comprises vanadyl-acetyl-acetonate and manganese acetate-tetrahydrate.

16. A process as claimed in claim 15, wherein said catalyst consists of molybdenum-hexacarbonyl.

17. A process as claimed in claim 4, wherein said catalyst comprises ammonium-metavanadate.

18. A process as claimed in claim 4, wherein said catalyst comprises vanadyl-acetyl-acetonate.

19. A process as claimed in claim 4, wherein said catalyst comprises freshly precipitated vanadium pentoxide.

20. A process as claimed in claim 4, wherein said catalyst is a cobalt catalyst.

21. A process as claimed in claim 4, wherein said catalyst is a manganese catalyst.

22. A process as claimed in claim 4, wherein said catalyst is a copper catalyst.

23. A process as claimed in claim 4, wherein said catalyst is a vanadium catalyst.

24. A process as claimed in claim 4, wherein said catalyst is a molybdenum catalyst.

25. A process as claimed in claim 4, wherein said catalyst consists essentially of cobalt, manganese, vanadium, their salts or oxides, or mixtures thereof.

26. A process as claimed in claim 25, wherein said catalyst further includes molybdenum, its salts, or its oxides in the range of 0.3 to 2 mg-atom/l.

27. A process according to claim 25, wherein said catalyst is introduced into said process with any cobalt and manganese therein being in the plus two oxidation state and with any vanadium therein being in the plus four or plus five oxidation state.

28. A process as claimed in claim 27, wherein said catalyst further includes molybdenum in the range of 0.3 to 2 mg-atom/l, introduced in the 0, +4, or +6 oxidation state.

29. A process as claimed in claim 27, which comprises a reaction temperature from 150° to 180° C.

30. A process as claimed in claim 25, which comprises said catalyst being from 0.8 to 20 mg-atom of cobalt or manganese per liter of carboxylic acid, from 0.4 to 20 mg-atom of vanadium per liter of carboxylic acid, or mixtures thereof.

31. A process as claimed in claim 30, which comprises said catalyst further including mixed therewith from 0.3 to 2 mg-atom of molybdenum per liter of carboxylic acid.

* * * * *